US005456919A

United States Patent [19]

Patell et al.

[11] Patent Number: 5,456,919

[45] Date of Patent: Oct. 10, 1995

[54] CAPSULE AND CAPLET COMBINATION

[75] Inventors: Mahesh Patell, Edison, N.J.; Gerard Frunzi, Jamaica Estates, N.Y.; F. Henry Merkle, Scotch Plains; Thomas Tencza, Wallington, both of N.J.

[73] Assignee: Bristol-Myers Squibb Company, New York, N.Y.

[21] Appl. No.: 231,941

[22] Filed: Apr. 21, 1994

Related U.S. Application Data

[63] Continuation of Ser. No. 893,476, Jun. 4, 1992, abandoned, which is a continuation-in-part of Ser. No. 459,032, Dec. 29, 1989, abandoned.

[51] Int. Cl.$^{6}$ .......... A61K 9/48

[52] U.S. Cl. .......... 424/451; 424/453; 424/454; 427/2.21; 427/2.22

[58] Field of Search .......... 424/451, 453, 424/454; 427/2.14, 2.16, 2.22, 3

[56] References Cited

U.S. PATENT DOCUMENTS

| | | | |
|---|---|---|---|
| 4,591,500 | 5/1986 | Scapinelli | 424/15 |
| 4,820,524 | 4/1989 | Berta | 424/474 |
| 4,851,230 | 7/1989 | Tencza | 424/467 |
| 4,928,840 | 5/1990 | Barshay | 220/8 |
| 4,936,074 | 6/1990 | Graham | 53/440 |
| 5,314,537 | 5/1994 | Berta | 118/30 |

*Primary Examiner*—D. Gabrielle Phelan

*Attorney, Agent, or Firm*—Anthony M. Santini; Charles J. Zeller

[57] ABSTRACT

A tamper-resistant dosage form capsule for the oral administration of therapeutic agents comprises a two-part capsule which is shrunk around a caplet so that the outer wall of the caplet is bound to the inner walls of both parts of the capsule. The caplet is placed into the capsule, and the dosage form is then subjected to relatively high humidity and temperature conditions, followed by drying the dosage form in a lower humidity environment, so that the capsule is shrunk to conform to the contours of the caplet and both parts of the capsule are bonded to the caplet.

18 Claims, 2 Drawing Sheets

CAPSULE AND CAPLET COMBINATION

RELATED APPLICATION

This application is a continuation of application Ser. No. 893,476, filed Jun. 4, 1992, now abandoned, which is a continuation-in-part of application Ser. No. 459,032, filed Dec. 29, 1989, now abandoned.

BACKGROUND OF THE INVENTION

1. Field of the Invention

The present invention relates to medicaments and more particularly to tamper-resistant capsules for the oral administration of therapeutic agents and to methods for the production of such capsules. Most specifically, the present invention concerns a pharmaceutical product wherein a capsule and a tablet contained within the capsule are brought into a tamper-resistant unitary association by treatment at high humidity and elevated temperature, followed by drying.

2. Description of the Related Art

At the present time many pharmaceutical compositions are dispensed in the form of capsules. Such capsules are generally elongated and cylindrical, and are often made of gelatin, starch, methyl cellulose, sugar-gelatin or gelatin-glycerin. The capsules are made in two separate parts, i.e., two semicapsules, one a cap and the other a body. The capsule may be filled with the pharmaceutical composition, generally a powder or liquid, and the capsule dosage form completed by placing the capsule cap over the capsule body.

Capsules are preferred by many consumers to other forms of medical dosage units, such as tablets, caplets (elongated tablets) or liquids. Capsules are popular because they do not have any taste and are easily swallowed. In comparison, a liquid may have a bitter or unpleasant taste and some persons have difficulty in swallowing tablets or caplets. In addition, capsule caps and bodies can be made in a variety of color combinations and sizes, are manufactured using automatic machines, and are filled by automatic capsule filling machines.

U.S. Pat. No. 4,928,840 entitled "Tamper Proof Encapsulated Medicaments" discloses a caplet adhesively bonded to the inner end surfaces of a capsule, such as a hard gelatin capsule. In one embodiment, an edible adhesive is placed on the ends of a caplet and the capsule is fitted over the caplet. According to claim 1 of the patent, the adhesive bonds the ends of the caplet to the internal ends of the capsule.

U.S. Pat. No. 4,936,074 entitled "Process For Preparing Solid Encapsulated Medicament" discloses a caplet enclosed in a capsule. In Example 10, cylindrical tablets are formed into capsules, capped and sealed in a microwave oven for 45 seconds, using methanol as a sealing or dielectric fluid.

U.S. Pat. No. 4,820,524 entitled "Gelatin Coated Caplets and Process for Making Same" discusses the widespread consumer preference for capsules. It also states that such powder filled capsules are not, by themselves, resistant to tampering and that the medicine in the capsule may be maliciously replaced by harmful look-alike substances. That patent suggests that a caplet may be made to look like and feel like a capsule by coating it with a gelatinous coating.

U.S. Pat. No. 4,591,500 entitled "Tablet Having the Shape of a Capsule, Process and Device for Its Preparation" describes a caplet having the shape of a gelatin capsule. The caplet incorporates granules or microgranules of an active substance and is made by compression of the composition on the tablet heads, i.e., in the longitudinal direction.

U.S. Pat. No. 4,851,230 entitled "Capsule Shaped Tablets" shows a pharmaceutical tablet (caplet) which is compressed into the shape of a capsule, including two heads (ogives) and a step at the junction of the two semicapsules.

The above-mentioned patents are incorporated by reference herein.

Generally caplets are formed by compressing the composition in the width direction (horizontally) which leaves a protruding band about the caplet. It has also been suggested that caplets may be compressed in the length direction (vertically) which leaves two ledge-like portions on the ends.

It would be possible to simply insert a conventional caplet in a capsule. That combined caplet-capsule is not tamper-resistant because the capsule may easily be opened and the caplet replaced with one that looks like it but is harmful.

SUMMARY OF THE INVENTION

In accordance with the present invention there is provided a capsule-caplet combination, in which the outer surface of a caplet inside a capsule is bound to the inner surfaces of the capsule to provide a relatively tamper-resistant dosage form produced at relatively low cost. There is also provided a method of producing such caplet-capsule combination using conventional automatic tableting and capsule filling machinery. The capsule-caplet is easily swallowed, like other capsules. The caplet may be enteric coated before inserting into the capsule, permitting the medicine to pass through the stomach and dissolve in the intestine.

The active medical ingredient is mixed with materials to form a compressible mass. In one embodiment, the powder mass is compressed on its ends to form a caplet without a band, or in a second embodiment the powder mass is compressed in width direction (horizontally), which leaves a protruding band about the caplet. The caplet is inserted into a pre-formed capsule body, and the capsule cap (the other half of the capsule) is then placed on the capsule body, closing the capsule. The capsule is formed from a water vapor permeable pharmaceutically acceptable and hydrothermally shrinkable material, for example, gelatin. The caplet and capsule sizes are chosen so that there is contact between the external wall of the caplet and the internal wall of the capsule. The capsule, with its internal caplet, is placed in a high humidity atmosphere with selected temperature conditions, causing the moisture content of the capsule to increase, whereby the capsule becomes soft and tacky. In such environment, the inner tacky surface of the capsule adheres to the external wall of the caplet. When the thus formed oral dosage unit is dried, the capsule loses moisture and shrinks tightly about the caplet, thereby providing a bond between the external wall of the caplet and the interior surface of the capsule. This phenomenon of capsule shrinkage caused by exposure to high humidity followed by dehumidification or drying is referred to herein as "hydrothermal contraction."

BRIEF DESCRIPTION OF THE DRAWINGS

The following detailed description of the invention should be taken in conjunction with the accompanying drawings. In the drawings.

DETAILED DESCRIPTION OF THE INVENTION

Figure 1:
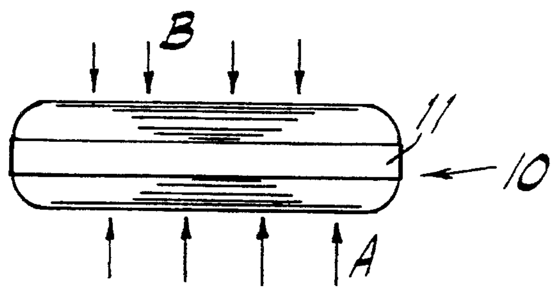
Fig. 1 (Prior Art)
FIG. 1 is a side plan view of a prior art caplet showing its external band.

As shown in FIG. 1, the conventional caplet 10 of the prior art is an elongated solid member formed from a pharmaceutical composition. It may be formed in a conventional automatic tableting machine. The caplet is generally formed by such machines by applying pressure on the sides, as shown by arrows A and B. This results in the formation of a protruding band 11, which is a ring-like protrusion about the longitudinal sides of the caplet.

Figure 2A:
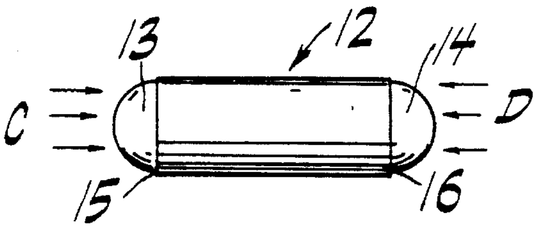
FIG. 2A is a side plan view of the caplet used in one embodiment of the present invention.
Figure 2B:
FIG. 2B is a top plan view of the caplet of FIG. 2A.

The caplet 12 utilized in one embodiment of the present invention is shown in FIGS. 2A and 2B.

Figure 3:
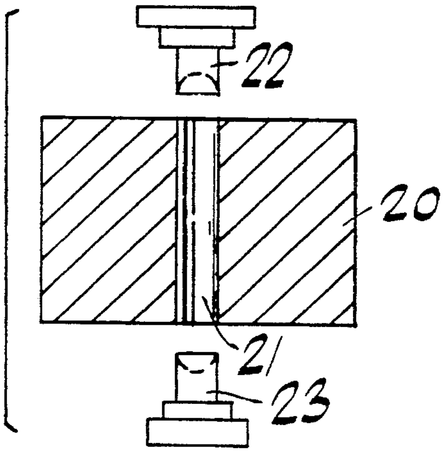
FIG. 3 is a side cross-sectional view of the machine used to compress the caplet shown in FIGS. 2A and 2B.

The caplet 12 is formed on automatic tableting machines, such as shown in FIG. 3. The pressure is applied vertically on the top and bottom cap portions 13, 14 as shown by arrows C and D. The caplet 12 does not have a protruding band on its external wall as in the caplet shown in FIG. 1. The caplet 12, due to the method of formation, has two annular flat ledge-like ring portions 15, 16 formed on its opposite cap portions 13, 14 respectively. As shown in FIG. 3, the die 20 has a cylindrical bore 21 into which the compressor members 22, 23 are inserted to compress the powder mass into a caplet. These vertically compressed caplets could be designed to fit snugly into different size hard shell gelatin capsules which are available in various sizes of #000 (largest) to 00, 0, 1, 2, 3 & 4 (smallest) regular or elongated sizes.

The vertically and horizontally compressed caplets are preferably formed so that their outer diameter closely approximates the internal dimensions of the capsules. This prevents the capsule shell from distorting during the bonding and packing processes and eliminates any voids and looseness of fit.

The size of the caplets, both as to their outer diameter and length, is selected to match the size of the capsules into which they are to be inserted. Thus, it is preferable that a portion of the side wall of each semicapsule be in close physical contact with the external side wall of the caplet, to ensure bonding of both the capsule body and the capsule cap to the caplet following treatment of the caplet-capsule combination in accordance with the process of the present invention. The minor portion of the capsule cap that overlays the minor portion of the capsule body is not bonded one to the other by the hydrothermal contraction of the present invention. Accordingly, it is preferred to incorporate a gelatin band or other secondary securing means at the capsule cap and capsule body interface, as hereinafter described.

Advantageously, the shrinkage of the capsule is uniform, so that there is little "blistering" of the capsule even at hard-to-adhere areas such as the rounded caplet ends, the protrusion band that exists on some caplets, or the shoulder that exists on other caplets. That is, the capsule assumes the external shape of the caplet very exactly, without substantial distortions.

The flat ring portions 15, 16 do not detract from the functioning of the caplet-capsule and do not present a problem as to consumer acceptance, since the caplet 12 is within a capsule.

The caplets of the present invention may be coated with a water-soluble film coating to provide a barrier for those active material agents that may adversely interact with the capsule material. Suitable materials are available which will absorb water and swell. The most common materials of this nature are cellulose derivatives, although high molecular weight proteins and synthetic polymers are also employed. Typically useful materials which can be utilized in the practice of this invention include methyl cellulose, hydroxypropyl methylcellulose available as "Methocel" (TM of Dow Chemical, Midland, Mich.); hydroxypropyl cellulose, available as "Klucel" (TM) from Aqualon Co; Povidone; sodium carboxymethyl cellulose; carboxymethyl cellulose; "Carbopol" (TM) water soluble gel forming polyacrylic resin available form B.F. Goodrich Chemical Co. and sorbitol.

If desired, an enteric material or covering may be coated on the caplet. The enteric coating is used to prevent the caplet from breaking up in the stomach so that the caplet passes through the stomach to the intestine, where it dissolves. A number of known enteric materials may be employed in the invention such as cellulose acetate phthalate, hydroxypropyl ethylcellulose and "Aquateric", i.e., a pseudo ethyl cellulose latex dispersion. A preferred enteric material is Eudragit L30D (TM), which is a copolymer that is anionic in character and based on polymethacrylic acid and polymethacrylic acid esters. This is described by the formula:

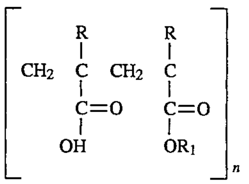

wherein:

n is the number reflecting the molecular weight of the polymer;

R is H or $CH_3$ and $R_1$ is $CH_3$ or $C_2H_5$ the ratio of free carboxyl group to ester groups is 1:1 and the mean molecular weight of the polymer is about 250,000. It is available from Rohm Pharma-GmbH.

Figure 4:
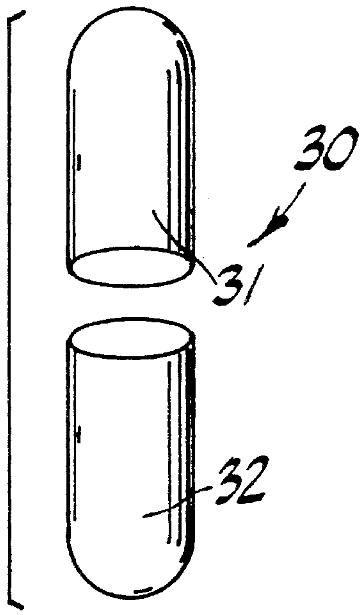
FIG. 4 is an exploded perspective view of a capsule.
Figure 5:
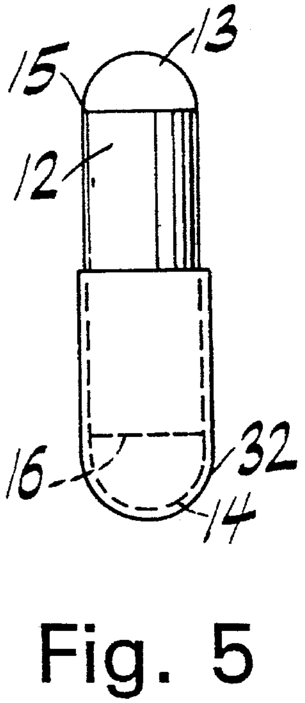
FIG. 5 is a side plan view of the caplet of FIG. 2A within a semicapsule.
Figure 6:
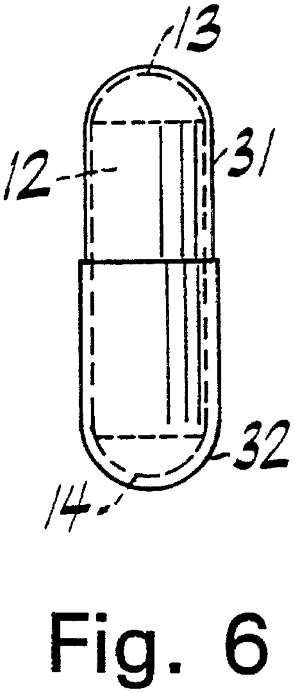
FIG. 6 is a side plan view of the complete caplet-capsule of one embodiment of the present invention.

The capsule 30 shown in FIG. 4, consists of two semicapsules 31, 32 each having a right-cylindrical tubular body portion and may be formed from commercially available capsule materials, such as are available from Elanco and Capsugel. The semicapsules 31,32 are smoothly surfaced so that the capsule cap 31 is freely slideable along the longitudinal axis of the capsule body 32. A suitable material for a capsule is gelatin although other useful capsules may be made of other materials including gelatin-glycerin, starch, gelatin-sugar, and methylcellulose.

The material selected for the formation of the capsule is pharmaceutically acceptable, hydrothermally shrinkable and water vapor permeable. Many high molecular weight proteins such as gelatins or carbohydrates like starches are suitable and are used to form capsules. The capsules may be of any selected color or combination of color. For example, one semicapsule may be blue and its joined semicapsule may be clear, or of a different color.

After the assembled caplet-capsule exits the capsule filling and closing machine, it is subjected to selected temperature/humidity conditions for an appropriate period of time so that at least the inner surfaces of the capsule assembled from the semicapsules become soft and tacky. The product is then dried to shrink the capsule tightly onto the caplet to produce a unitary structure which is in medical dosage form suitable for animal or human use.

To ensure uniform shrinkage without blistering or other distortions of the capsule, the caplet and capsule dimensions are selected to provide an essentially exact fit, i.e., there should be minimal void space within the capsule prior to the start of the hydrothermal contraction process. Additionally, the capsule cap and capsule body length dimensions should be such that sufficient contact is made between the side wall of the caplet and the corresponding interior surfaces of the cap and body. It has also been found that any vapor formed within the capsule during the process is released from between the semicapsules.

Hydrothermally contractable materials are materials which will increase their equilibrium moisture content under appropriate temperature/humidity conditions and permanently contract when dried, i.e., dehumidified. The hydrothermally contractable materials employed in this invention become soft and tacky as their moisture content increases. As contraction occurs due to a subsequent loss in moisture content, a bond is formed between the caplet and the capsule so that the caplet cannot be replaced without materially and visibly altering the appearance of the capsule.

Typically, the equilibrium moisture value of the capsule forming materials employed in this invention is about 14% to 16%. A modest increase in the moisture content of the material above 16%, for example, up to about 20%, especially up to about 18%, results in a capsule that is soft and tacky, as previously mentioned.

The moisture content of the capsule can be increased by exposing the product to high humidity conditions and especially to such high humidity conditions at elevated temperatures. The optimum relative humidity condition will depend on other factors, however, such as the nature of the capsule material, the temperature at treatment and the duration of exposure. Time is not critical and will vary with the material chosen and the selected temperature and relative humidity conditions. The only requirement is that the caplet-capsule combination be exposed, at the process operating conditions of temperature and humidity, for a time sufficient to effect the increase in capsule moisture content. Thus, the exposure time may be as low as about 5 minutes or as long as about 24 hours. Higher relative humidity and temperature conditions will favor the shorter periods.

Typically, the temperature range is from about 25° to 75° C., preferably 30° C. to 55° C. Typically, the relative humidity is from about 30% to about 100%, preferably from about 75% to 100%, most preferably from about 75% to about 90%. A temperature of 30° C. to 45° C. with a relative humidity within the range of 75% to 90% is suitable.

After treatment under the selected humidification conditions, the products are dried to complete the hydrothermal contraction process. The conditions for drying and storing are from about 10° C. to 30° C. at a relative humidity up to about 70%, preferably 30% to 60%, although drying at ambient conditions is suitable.

The most important consideration for the practice of this invention is that the capsule forming material selected by hydrothermally shrinkable to form a bond between the caplet and the capsule. The optimum humidity, temperature and time conditions for the production of the products of the invention can be easily selected by a few simple tests based on the information provided in this disclosure.

The preferred procedure for effecting the hydrothermal shrinkage is to select a water vapor permeable material and expose it to an atmosphere of high relative humidity.

In the embodiments illustrated in the examples below, the moisture content of the semicapsules is increased, resulting in a relaxation of the gelatin molecules of the semicapsules. The moisture content of the capsules is increased by placing the caplet filled capsules in an environment of from about 25° C. to about 75° C. and a relative humidity of from about 30% to about 100% during a period of about 5 minutes to about 24 hours, typically less than 12 hours. Suitable ranges are about 40° C. to about 55° C. and a relative humidity of about 50% to about 100% and especially the range of about 60% to about 90% RH and most especially a range of over 75% relative humidity, during a period of about 5 minutes to about 4 hours.

The caplet is inserted into the body of the semicapsule, which is then covered with the untreated capsule cap. The caplet-capsule assembly is raised in its moisture content as described above, and then dried to reduce its moisture content, so that the capsule tightly encloses and adheres to the caplet.

The subsequent reduction in moisture content of the humidified capsule can be accomplished, for example, by storage for a time at ambient, or preferably by drying under low humidity conditions. It is believed that the hydrothermal contraction phenomenon is caused by a change in capsule material molecular orientation. The preferred conditions for drying and storing are a temperature of 10° C. to 30° C. and a relative humidity (RH) of less than 70%, most preferably 30% to 60%, for a period of time sufficient to cause shrinkage of the capsule onto the caplet. Preferably, after completion of the process, the moisture content of the capsule is essentially the same as existed prior to treatment. Excessive drying is not recommended, as the capsule becomes too brittle and is thus prone to cracking.

The hydrothermal contraction treatment can be performed in various types of equipment or in a chamber to provide the necessary treatment conditions. Equipment which may be used includes a tablet coating pan, a capsule banding machine, a portion of a capsule banding machine, a fluid bed dryer/granulator, or trays in a room or a chamber which can be temperature and humidity controlled.

While this invention has been described principally as applied to caplets such as caplet 12, it will be apparent to those skilled in the art that it is equally applicable to caplets such as caplet 10 which has a longitudinal protruding band. Moreover, the process of the present invention is not meant to be limited solely to cylindrically shaped caplets. Thus, the term "caplet" should be read broadly to encompass solid dosage form of other geometric configurations, e.g., round, oval, etc. Of course, it would be necessary to provide the corresponding appropriately shaped semicapsules. It is not believed that such other geometric forms are outside the scope of conventional capsule technology.

If desired, at least a partial band of gelatin, or other swallowable material, may be fastened to the caplet filled capsule at the cap/body juncture to provide additional tamper resistance. In the event of tampering, the removal of the band from a capsule would be easily recognized by the consumer. In addition, or alternatively, a band of water-alcohol solution may be applied at the capsule body-capsule cap junction following the completion of the hydrothermal contraction process. The solution, by capillary action, flows between the overlapped portions of the semicapsules and, when dried, bonds these overlapped portions.

EXAMPLE I

A combination of analgesic ingredients consisting of 500 mg. of acetaminophen and 65 mg of caffeine was compressed into a cylinder with rounded ends using special shaped tooling. The caplet dimensions were: length 0.826" and diameter 0.262". This caplet shape was designed and selected to provide an exact fit to match the inner dimensions of a #0 hard gelatin capsule shell.

Both uncoated and or film coated core caplets were inserted into empty hard gelatin capsule shells by hand and the cap and body shells were closed to form closed capsules. The closed capsules were then subjected to an environmental condition of 90% (relative humidity) at 48° C. in a temperature/humidity chamber for a period of one hour. This treatment allowed the caplet filled gelatin shells to increase their moisture to a higher moisture content of approximately 18%.

The treated capsules were removed from the temperature/humidity chamber and allowed to reequilibrate on a laboratory bench top to ambient temperature and humidity conditions in a controlled environment. This process of reequilibration or moisture loss caused the capsule shells, both the body and cap, to contract and shrink to the contours of the core caplet and resulted in a permanent bond between the inner surfaces of the capsule shell and the core caplet as well as bonding the overlapped cap and body portions of the capsule shell.

A gelatin band, which acts as a seal, was then applied at the junction of the two semi-capsules. The gelatin seal is an invisible band of gelatin, forming a tamper-resistant band, which may be automatically applied at high production speeds. A suitable band applying machine is the "Quali-seal" (TM) capsule sealing machine, available from ELANCO Qualicaps, Indianapolis, Ind. The gelatin band could be colored using different dyes for visual color effects.

EXAMPLE II

The caplets were formed as in Example 1, on a conventional tablet press and commonly used tablet tooling with the compression force applied horizontally as is normally done. The caplet dimensions were length 0.750" and a diameter (thickness) of 0.250" to 0.255" for size #0 capsule shell. Similarly, smaller or larger size caplets could be designed to fit smaller size capsules like size #1, 2, 3, 4, or large size capsules such as size #00, 000 etc. The caplets compressed in this manner have a band (protrusion or "belly band") which formed a complete ring about the caplet, as shown in the caplet of FIG. 1. These caplets, either coated or uncoated, are inserted in the capsule shell and when the capsules are shrunk onto the caplet the capsules retain the shape of the caplets, so that the resulting filled capsules have protruding bands. The hydrothermal contraction conditions and banding means were the same as Example I.

A combination of the analgesic ingredients consisting of 500 mg of acetaminophen and 65 mg caffeine or an analgesic combination of 250 mg of acetaminophen, 250 mg of aspirin and 65 mg of caffeine and a combination of analgesic with a sleep aid consisting of 500 mg of acetaminophen and 38.355 mg of diphenhydramine monocitrate were compressed into the above-mentioned caplet dimensions to fit size #0 capsule shells.

EXAMPLE III

An analgesic caplet containing 500 mg of aspirin was formed as in Example II. These caplets were then enteric coated using standard enteric coating solution containing Eudragit L 30 D, an enteric polymer. These enteric coated caplets were inserted into the capsule shells. The hydrothermal contraction treatment conditions and the banding process were the same as in Example I.

EXAMPLE IV

The caplets were formed as described in Example II and inserted into capsules. The capsules were then treated to obtain hydrothermal contraction by subjecting them to an environmental condition of 90% RH at 60° C. in a temperature/humidity chamber for a period of 10 minutes. Treated capsules were then banded as described in Example I.

EXAMPLE V

The capsules were formed as in Example IV, except that the treatment conditions were 90% RH at 35° C. for 8 hours.

EXAMPLE VI

The capsules were formed and hydrothermally contracted as in Example III. However, the caplets were sprayed with a different solution, namely, Carbopol 934-P, 2 grams, water 178 grams and ethanol 20 grams, before insertion into the capsule. This mixture was warmed to completely dissolve the Carbopol and then sprayed onto the caplets.

EXAMPLE VII

The caplets were formed and treated as described in Example II, except that the capsule banding solution which normally contains gelatin, Tween 20 and water was modified to contain bonding agents such as Eudragit L 30 D, Carbopol, Methocel, etc., at a level of 1% to 5%.

We claim:

1. A method of forming a tamper-resistant oral dosage unit in which a caplet containing at least one medicinally active ingredient is enclosed in a capsule comprising a body semicapsule and a cap semicapsule, each having an inner surface, and each formed of a pharmaceutically acceptable, water vapor permeable, hydrothermally shrinkable material, comprising the steps of:

(a) preparing a caplet having outer surfaces;

(b) enclosing the caplet within the semicapsules to form a capsule-caplet combination unit;

(c) exposing said unit to temperature and humidity conditions effective to increase the moisture content of the capsule material;

(d) drying said unit, whereby the capsule hydrothermally shrinks around the caplet, and the outer surface of the caplet is unitarily bound to the inner surfaces of the capsule.

2. A method as in claim 1 wherein the humidity is from about 30% to about 100% and the temperature is from about 25° C. to about 75° C.

3. A method of forming a tamper-resistant oral dosage unit in which a caplet containing at least one medicinally active ingredient is enclosed in a water vapor permeable capsule, consisting of a capsule body and a capsule cap, comprising the steps of:

(a) enclosing the caplet within the capsule;

(b) raising the moisture content of the capsule by exposing the capsule-caplet combination to an environment of higher humidity, between about 30% and about 100% relative humidity, at a temperature of from about 25° C. to about 75° C. for a period of about 5 minutes to about 24 hours, and (c) thereafter reducing the moisture content of the capsule by drying the humidified capsule-caplet combination of (b) above in an environment of lower humidity, (d) said capsule thereby hydrothermally contracting about the contours of the caplet wherein the capsule cap and capsule body are unitarily bound to said caplet, to provide tamper-resistance to said oral dosage unit.

4. The method of claim 3 wherein the relative humidity is from about 50% to about 100% and the temperature is from about 30° C. to about 55° C.

5. The method of claim 4 wherein the relative humidity is from about about 50% to about 100% and the temperature is from about 40° C. to about 50° C.

6. The method of claim 3 including the step of coating an enteric material on the surface of the caplet before it is enclosed in the capsule.

7. The method of claim 3 wherein the lower humidity environment is at a temperature of from about 10° C. to about 30° C.

8. The method of claim 3 wherein the caplet further comprises a water-soluble film coating.

9. A method of forming a tamper-resistant oral dosage unit in which a caplet containing at least one medicinally active ingredient is enclosed in an edible, water vapor permeable, and non-toxic capsule comprising the steps of:

(a) preparing a caplet;

(b) enclosing the caplet within said non-toxic capsule;

(c) exposing the thus formed capsule-caplet combination to an environment of higher humidity in the range of about 60% to about 100% and a higher temperature range of about 25° C. to about 75° C., and (d) thereafter drying the capsule-caplet combination at a lower humidity of about 30% to about 60% and at a temperature of about 10° C. to about 30° C.

10. The method of claim 9 wherein the higher temperature range is from about 40° C. to about 55° C.

11. The method of claim 9 wherein the exposure of the capsule-caplet combination in the higher humidity environment is from about 5 minutes to about 24 hours.

12. The method of claim 9 wherein the higher humidity environment is at a humidity of from about 75% to about 90% and at a temperature of from about 30° C. to about 45° C.

13. A tamper-resistant oral dosage unit produced by the process of claim 1.

14. A tamper-resistant oral dosage unit produced by the process of claim 3.

15. A tamper-resistant oral dosage unit produced by the process of claim 9.

16. The method of claim 1 wherein the capsule material is selected from the group consisting of gelatins and carbohydrates.

17. The method of claim 3 wherein the capsule is formed from a material selected from the group consisting of gelatins and carbohydrates.

18. The method of claim 9 wherein the capsule is formed from a material selected from the group consisting of gelatins and carbohydrates.

* * * * *